(12) United States Patent
Nickerson et al.

(10) Patent No.: US 8,936,723 B2
(45) Date of Patent: Jan. 20, 2015

(54) CHROMATOGRAPHY COLUMN WITH LARGE DIAMETER END FITTING OPENINGS

(75) Inventors: Mark A. Nickerson, Landenberg, PA (US); Frank Marsden Willis, Deptford, NJ (US); William Barber, Landenberg, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1129 days.

(21) Appl. No.: 12/552,837

(22) Filed: Sep. 2, 2009

(65) Prior Publication Data

US 2011/0049030 A1 Mar. 3, 2011

(51) Int. Cl.
*G01N 30/60* (2006.01)
*B01D 15/22* (2006.01)

(52) U.S. Cl.
CPC .......... *G01N 30/6026* (2013.01); *B01D 15/22* (2013.01)
USPC ....................... 210/198.2; 210/656

(58) Field of Classification Search
CPC ............................ G01N 30/6026; B01D 15/22
USPC ............. 210/198.2, 635, 656; 96/101; 422/70
See application file for complete search history.

(56) References Cited

U.S. PATENT DOCUMENTS

| | | | | |
|---|---|---|---|---|
| 3,771,659 A * | 11/1973 | Fraser | ........................ | 210/198.2 |
| 4,557,830 A * | 12/1985 | Onitsuka et al. | ........... | 210/198.2 |
| 4,582,608 A * | 4/1986 | Ritacco | ......................... | 210/656 |
| 4,587,014 A * | 5/1986 | America | ..................... | 210/198.2 |
| 4,732,687 A * | 3/1988 | Muller et al. | ................. | 210/656 |
| 4,755,293 A * | 7/1988 | Sakamoto et al. | ......... | 210/198.2 |
| 4,876,005 A * | 10/1989 | America | ..................... | 210/198.2 |
| 4,888,112 A * | 12/1989 | Kronwald | .................. | 210/198.2 |
| 4,894,152 A * | 1/1990 | Colvin et al. | .............. | 210/198.2 |
| 5,009,778 A * | 4/1991 | Nickerson et al. | ......... | 210/198.2 |
| 5,178,767 A * | 1/1993 | Nickerson et al. | ......... | 210/656 |
| 5,194,225 A * | 3/1993 | Muller et al. | ................... | 422/70 |
| 5,227,059 A * | 7/1993 | Shepherd | ................... | 210/198.2 |
| 5,324,426 A * | 6/1994 | Joseph et al. | .............. | 210/198.2 |
| 5,378,361 A * | 1/1995 | Baeckstrum | ............... | 210/198.2 |
| 5,611,904 A * | 3/1997 | Cole et al. | ..................... | 204/640 |
| 5,667,676 A * | 9/1997 | Alaska | ........................ | 210/198.2 |
| 5,693,223 A * | 12/1997 | Yamada et al. | ............ | 210/198.2 |
| 5,772,875 A * | 6/1998 | Pettersson et al. | ......... | 210/198.2 |
| 6,224,760 B1 * | 5/2001 | Davies et al. | .............. | 210/198.2 |
| 7,101,477 B1 * | 9/2006 | Willis et al. | ................ | 210/198.2 |
| 7,208,085 B2 * | 4/2007 | Geng et al. | ................. | 210/198.2 |
| 2005/0199540 A1 * | 9/2005 | Zelechonok et al. | ...... | 210/198.2 |
| 2007/0029241 A1 | 2/2007 | Willis et al. | | |
| 2007/0029791 A1 | 2/2007 | Haertl | | |
| 2007/0295663 A1 | 12/2007 | Iraneta et al. | | |
| 2010/0181240 A1 * | 7/2010 | Rahn et al. | ................. | 210/198.2 |

* cited by examiner

*Primary Examiner* — Ernest G Therkorn

(57) ABSTRACT

A column for use in chromatography, the column having a tube with a bore that can contain a packing medium captured between two porous plugs positioned at opposite ends. End fittings are attached to the tube ends, the end fittings having a duct with a duct opening having a diameter at least as large as the diameter of the tube bore which it faces. The duct opening may be positioned within a recess in spaced apart relation to the porous plugs to prevent the end fitting from contacting the plug and burnishing its surface.

18 Claims, 5 Drawing Sheets

CHROMATOGRAPHY COLUMN WITH LARGE DIAMETER END FITTING OPENINGS

FIELD OF THE INVENTION

This invention relates to columns useful in chromatography, such as high performance liquid chromatography, and especially to such columns with structures providing improved flow characteristics for improved column performance.

BACKGROUND

High performance liquid chromatography (HPLC) is a process by which one or more compounds from a chemical mixture may be separated and identified. A transport liquid, for example a solvent, is pumped under high pressure through a column of packing medium, and a sample of the chemical mixture to be analyzed is injected into the column. As the sample passes through the column with the liquid, the different compounds, each one having a different affinity for the packing medium, move through the column at different speeds. Those compounds having greater affinity for the packing material move more slowly through the column than those having less affinity, and this speed differential results in the compounds being separated from one another as they pass through the column.

The transport liquid with the separated compounds exits the column and passes through a detector, which detects the molecules, for example by spectrophotometric absorbance measurements. A two dimensional plot of the detector measurements against elution time or volume, known as a chromatogram, may be made, and from the chromatogram the compounds may be identified.

For each compound, the chromatogram displays a curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, are undesirable as they may allow minor components of the mixture to be masked by major components and go unidentified.

Columns for HPLC typically comprise high strength stainless steel tubes packed under high pressure with packing media comprising, for example, silane derivatized silica spheres having a diameter less than 20 microns. The packing media is held within the tube by sintered stainless steel frits. The frits are porous plugs that allow the transport liquid and the sample to pass through the tube while retaining the packing medium. It is advantageous to press the frits into the bore of the tube with an interference fit to prevent the packing material from escaping past the frits. Threaded end fittings are positioned at opposite ends of the tube. The end fittings keep the frits within the bore, compress the packing media to help maintain its hydraulic orientation, and are adapted to receive standard fittings from capillary tubes for connecting the column to a chromatograph.

Dead space within a column should be avoided because it allows mixing of the transport liquid and the sample which degrades column performance. This manifests itself as a broadening of the peaks and a concomitant decrease in the resolving capability of the HPLC apparatus. In prior art columns dead space was reduced by making the outlet of the end fitting which interfaces with the tube small relative to the tube inlet, thereby reducing the volume between the end fitting and the tube. However, this results in contact between the end fitting and the frit at the tube inlet, which burnishes the frit, reduces its wetted area, and disrupts the continuity of the flow. These factors contribute to a degradation of column performance. There is clearly a need for a column which avoids these disadvantages while still reducing dead space within the column.

DETAILED DESCRIPTION

Figure 1:
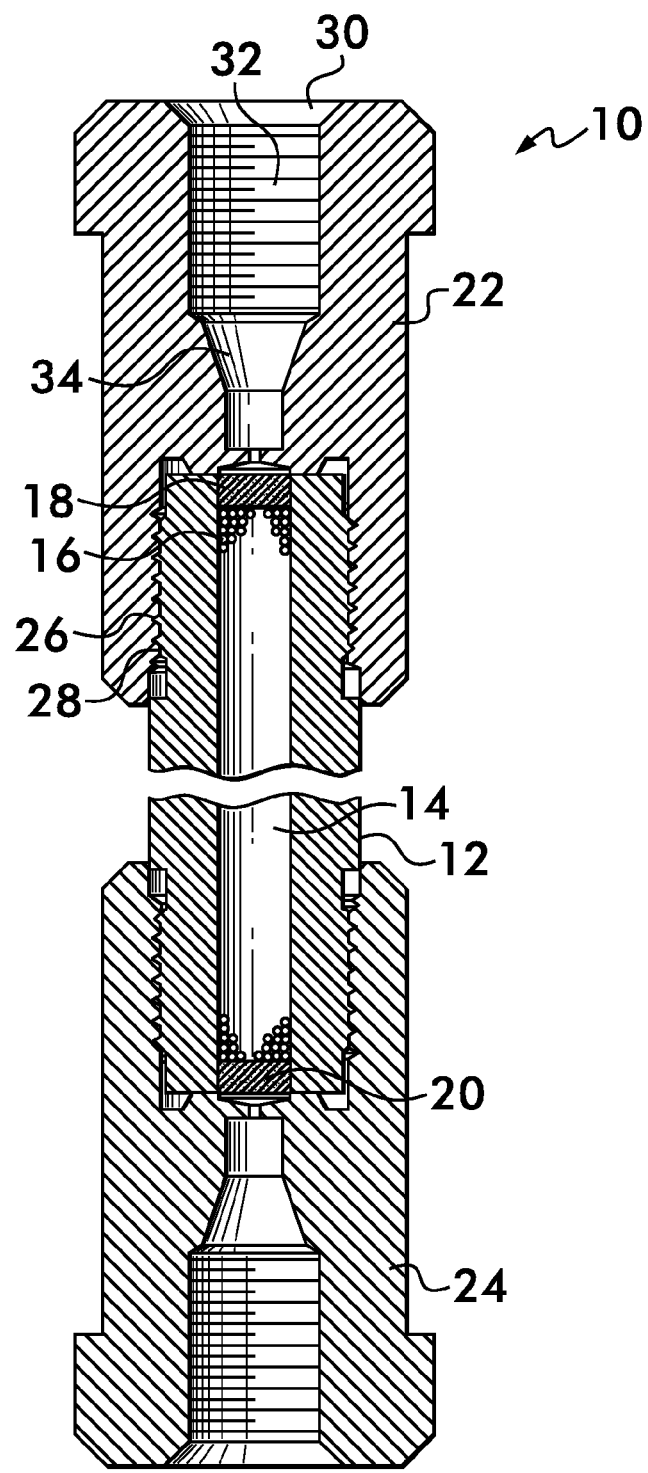
FIG. 1 is a longitudinal sectional view of a column according to the invention.

The invention concerns a column for chromatography. In one example embodiment, the column comprises a tube having a bore therethrough, the bore having a diameter. A first porous plug may be located within the bore at a first end of the tube. A first fitting is attached to the first end of the tube. The first fitting has a duct positioned therein. The duct has a first opening positionable in facing relation with the first porous plug. The first opening has a diameter at least about equal to the tube bore diameter. The first opening is positioned within a recess in the first fitting there by positioning the first opening in spaced apart relation away from the first porous plug.

The duct also has a second opening positioned in spaced apart relation to and facing the first opening. The second opening may have a diameter less than the diameter of the first opening. In this embodiment, the duct further comprises a surface positioned between the first and second openings. The surface may be conical. The conical surface may have a cone angle, for example, from about 150° to about 175°.

The first fitting may further comprise a conduit in fluid communication with the second opening. When present the conduit may have an inner diameter about equal to the diameter of the second opening.

In one embodiment the first fitting is theadedly attached to the tube. The column may also comprise a seal positioned between the first fitting and the tube. In an alternate embodiment, the first fitting may comprise a first sealing surface surrounding the recess. In this embodiment a second sealing surface surrounds the bore at the first end of the tube. The first sealing surface contacts the second sealing surface and forms a seal between the first fitting and the tube.

In certain embodiments the first duct may be integrally formed with the first fitting. Alternately, the first duct and the first fitting may belong to two different pieces. For example, the first fitting may comprise a compression nut threadedly attached to the tube, and a compression body captured between a surface of the compression nut and a surface of the tube surrounding the bore at the first end of the tube. In this embodiment the duct is located in the compression body.

The column according to the invention may also comprise a second porous plug located within the tube bore at a second end of the tube. A second fitting may be attached to the second end of the tube. The second fitting may have a second duct positioned therein. The second duct may have a first opening in facing relation with the second porous plug. The first opening of the second duct may also have a diameter at least about equal to the bore diameter. The first opening of the second duct may be positioned within a recess in the second fitting and thereby in spaced apart relation away from the second porous plug.

The second duct has a second opening positioned in spaced apart relation to and facing the first opening of the second duct. In some embodiments the second opening of the second duct may have a diameter less than the diameter of the first opening of the second duct. In these embodiments the second duct comprises a surface positioned between the first and second openings. The surface may be conical. The conical surface may have a cone angle, for example, from about 150° to about 175°.

In certain embodiments the second fitting further comprises a second conduit in fluid communication with the second opening. The second conduit may have an inner diameter about equal to the diameter of the second opening.

The column may also include a packing medium located within the bore.

In another embodiment of a column for chromatography, the column comprises a tube having a bore with a bore inlet at one end and a bore outlet at an opposite end. A first porous plug is positioned within the bore at the one end, and a second porous plug is positioned within the bore at the opposite end. A packing medium may be contained within the bore. A first fitting is attached to the tube at the one end. The first fitting has a first duct positioned therein in fluid communication with the bore. The first duct has an outlet facing the bore inlet. The outlet has a diameter at least about equal to the diameter of the bore. The outlet is furthermore positioned within a recess in the first fitting, in spaced apart relation away from the first porous plug. A second fitting is attached to the tube at the opposite end. The second fitting has a second duct positioned therein in fluid communication with the bore outlet. The second duct has an inlet facing the bore outlet. The inlet has a diameter at least about equal to a diameter of the bore. The inlet is positioned within a recess in the second fitting in spaced relation away from the second porous plug.

In one embodiment the first duct comprises a first conical surface and the second duct comprises a second conical surface. The first and second fittings may be threadedly attached to the tube. Furthermore, the first duct may be integrally formed with the first fitting and the second duct may be integrally formed with the second fitting.

FIG. 1 shows an example of a liquid chromatography column 10 according to the invention. Column 10 may be any type of column used in liquid chromatography, examples of which include a microbore column, an analytical column, a preparatory column and a guard column. The columns may be of any suitable size, for example, inner diameters that range, for example, between about 1 mm and about 22 mm inclusive, and lengths up to, for example, about 30 cm.

Column 10 includes a tube 12 which defines a bore 14 that may contain a packing medium 16 used in liquid chromatography, for example, silane derivatized silica spheres having a diameter of less than 20 microns. The packing medium 16 is packed under high pressure and may be held in place by porous plugs 18 and 20 that are inserted into bore 14 at opposite ends of tube 12. Plugs 18 and 20 may be, for example, sintered stainless steel frits with pores less than the diameter of the packing medium 16.

Compression nut end fittings 22 and 24 may be threadedly attached to opposite ends of the tube 12, the tube having external threads 26 which engage internal threads 28 in the end fittings in this embodiment. The end fittings may further comprise a port 30 with internal threads 32 and a tapered section 34 designed to receive standard fittings of a capillary tube (not shown) for connection of the column 10 to a liquid chromatograph.

Figure 2:
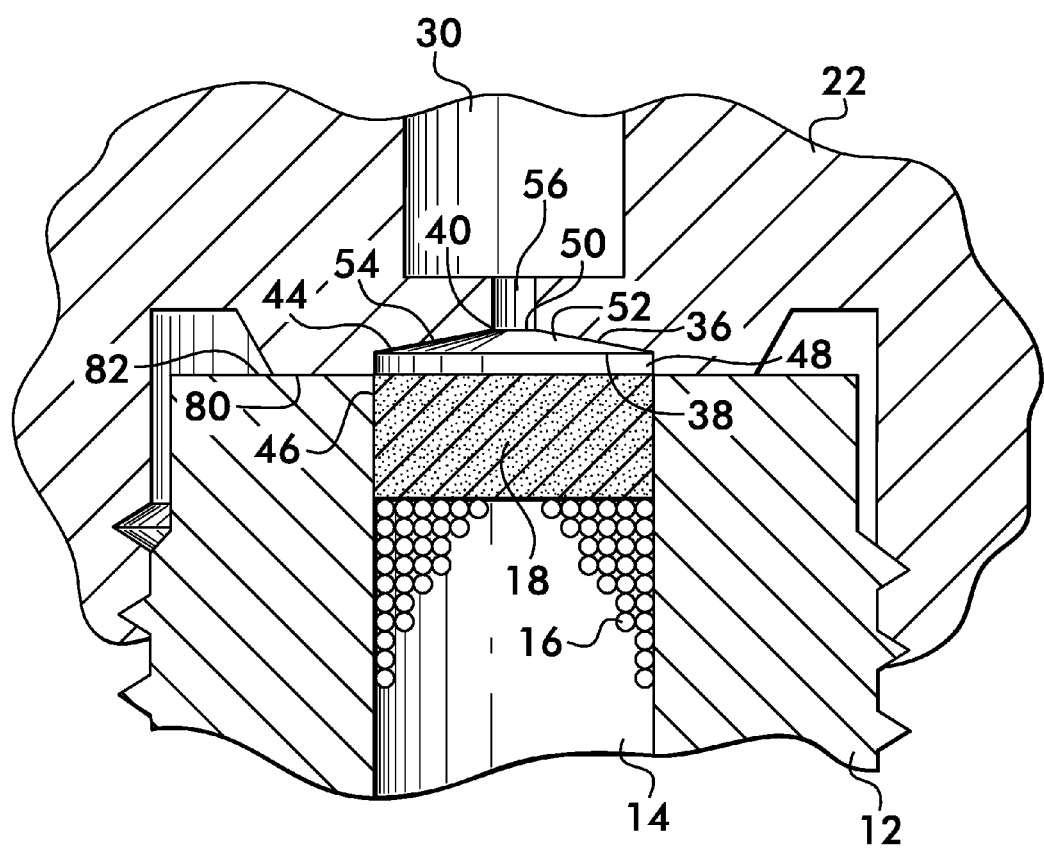
FIGS. 2 and 3 are longitudinal sectional views which show the end portions of the column shown in FIG. 1 on an enlarged scale.

When end fitting 22 is connected to the chromatograph to receive the transport liquid containing the sample compound to be analyzed, it may be regarded as an intake fitting. As shown in FIG. 2, intake fitting 22 comprises an intake duct 36 having a first opening, which may be referred to as intake duct outlet 38, and a second opening, which may be called an intake duct inlet 40. Intake duct outlet 38 is positioned in facing relation with the porous plug 18 positioned within bore 14 at an end of tube 12. The intake duct outlet 38 has a diameter 44 at least as large as the diameter 46 of the bore 14. Furthermore, the intake duct outlet 38 is positioned within a recess 48 in the intake fitting 22, thereby locating the outlet 38 in spaced apart relation away from the porous plug 18. These two features cooperate to ensure that the end fitting 22 does not contact the porous plug 18 when the end fitting is tightened onto the tube 12. The porous plug is relatively delicate and easily burnished by contact with the end fitting. If the end fitting is permitted to contact the porous plug 18 it disrupts the pores and thereby disrupts the continuity of the flow through the column 10, degrading column performance. The features also permit the full surface area of the plug to be wetted, thereby improving distribution of the transport liquid and the sample compound to the packing medium 16 within the column. The intake duct outlet diameter 44 may range from a value at least about equal to the bore diameter to about 0.01 inches greater than the bore diameter, and the depth of recess 48 may range, for example, from about 0.001 inches to about 0.004 inches.

The intake duct inlet 40 has a diameter 50 less than the intake duct outlet diameter 44. The intake duct inlet diameter 50 may range, for example, from about 0.01 inches to about 0.014 inches. To maintain as small a duct volume as possible within the intake fitting 22 and reduce the dead space there is a surface 52 which extends between the intake duct inlet 40 and the intake duct outlet 38. Surface 52 may be conical in shape. The surface may for example, have a cone angle 54 from about 150° to about 175°, with some embodiments having cone angles of about 160° to about 175°, additional embodiments having cone angles of about 165° to about 175°, and other embodiments having cone angles of about 170° to about 175°. The intake fitting further comprises a conduit 56 which provides fluid communication between the intake duct inlet 40 and the port 30 which receives the capillary tube from the chromatograph (not shown). Conduit 56 has an inner diameter about equal to the diameter 50 of the intake duct inlet to further limit dead space within the column 10.

Figure 3:
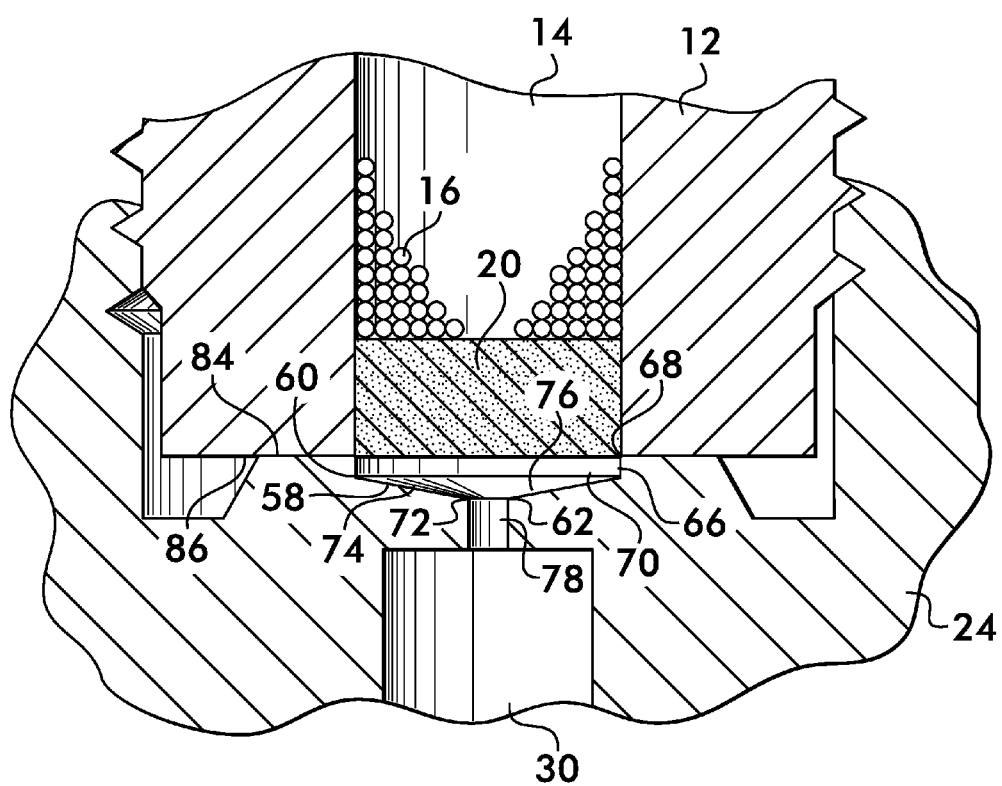

As shown in FIG. 3, end fitting 24 may have the same structure as the intake fitting 22. This structural symmetry permits either end of the column to be attached to the chromatograph and still achieve improved performance. However, when end fitting 22 is connected to the chromatograph to receive a transport liquid containing the sample compound to be analyzed as described above, the end fitting 24 may be regarded as an exit fitting, positioned at the opposite end of the tube 12 where the sample compound and transport liquid exit the column 10 and proceed to a detector for example.

As shown in FIG. 3, exit fitting 24 comprises an exit duct 58 having a first opening, referred to as an exit duct inlet 60, and a second opening, referred to as an exit duct outlet 62. Exit duct inlet 60 is positioned in facing relation with the porous plug 20 positioned within bore 14 at the opposite end of tube 12. The exit duct inlet 60 has a diameter 66 at least as large as the diameter 68 of the bore 14. Furthermore, the exit duct inlet 60 is positioned within a recess 70 in the exit fitting 24, thereby locating the exit duct inlet 60 in spaced apart relation away from the porous plug 20. As with the intake fitting 22, these two features cooperate to ensure that the end fitting 24 does not contact the porous plug 20 when the end fitting is tightened onto the tube 12. The porous plug is relatively delicate and easily burnished by contact with the end fitting. If the end fitting is permitted to contact the porous plug 20 it disrupts the pores and thereby disrupts the continuity of the flow through the column 10, degrading column performance. The features also permit the full surface area of the plug to be wetted, thereby improving evacuation of the transport liquid and the sample compound from the bore 14 of the tube 12. The exit duct inlet 60 has a diameter 66 that may range from a value at least about equal to the bore diameter, to about 0.01 inches greater than the bore diameter, and the depth of recess 70 may range, for example, from about 0.001 inches to about 0.004 inches.

The exit duct outlet 62 has a diameter 72 less than the exit duct inlet diameter 66. The exit duct outlet diameter 72 may range, for example, from about 0.01 inches to about 0.14 inches. To maintain as small a volume as possible within the exit fitting 24 and reduce the dead space there is a surface 74 which extends between the exit duct outlet 62 and the exit duct inlet 60. Surface 74 may be conical in shape. The surface may, for example, have a cone angle 76 from about 150° to about 175°, with some embodiments having cone angles of about 160° to about 175°, additional embodiments having cone angles of about 165° to about 175°, and other embodiments having cone angles of about 170° to about 175°. The exit fitting 24 further comprises a conduit 78 which provides fluid communication between the exit duct outlet 62 and the port 30 which receives a capillary tube of the chromatograph (not shown). Conduit 78 has an inner diameter about equal to the diameter 72 of the exit duct outlet to further limit dead space within the column 10.

FIGS. 1-3 illustrate embodiments of the invention wherein the intake and exit ducts 36 and 58, as well as the conduits 56 and 78 are integrally formed with the end fittings 22 and 24. FIGS. 1-3 further illustrate a metal to metal seal between the end fittings 22 and 24 and the tube 12. As shown in FIG. 2, the metal to metal seal is formed by a first sealing surface 80 positioned on the end fitting 22 surrounding the recess 48, and a second sealing surface 82 surrounding the bore 14 at the end of the tube 12. Upon tightening of the fitting 22 onto the tube 12 the first and second sealing surfaces 80 and 82 are brought into contact to form a metal to metal seal between the end fitting 22 and the tube 12. FIG. 3 shows a similar metal to metal seal arrangement wherein a second metal to metal seal is formed by a first sealing surface 84 positioned on the end fitting 24 surrounding the recess 70, and a second sealing surface 86 surrounding the bore 14 at the opposite end of tube 12. Upon tightening of the fitting 24 onto the tube 12 the first and second sealing surfaces 84 and 86 are brought into contact to form a metal to metal seal between the end fitting 24 and the tube 12.

Figure 4:
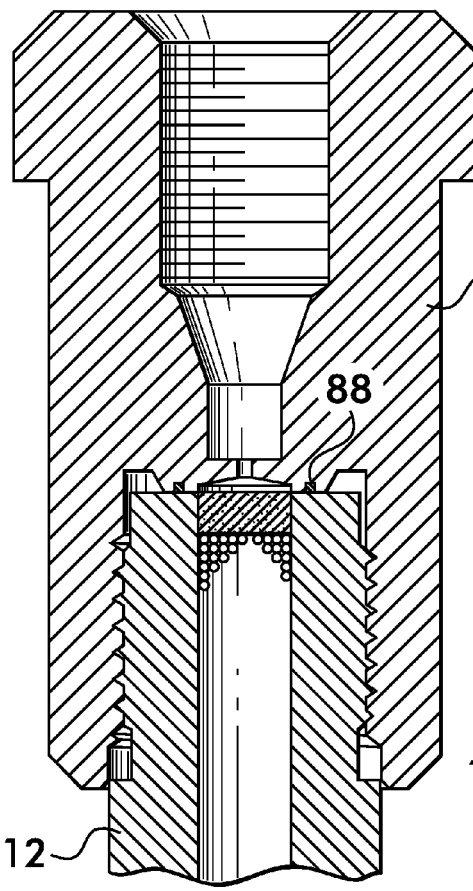
FIGS. 4 through 6 are partial longitudinal sectional views illustrating alternate embodiments of the column according to the invention.

It may be desirable to use the end fittings 22 and 24 having the integrally formed intake and/or exit ducts 36 and 58 in conjunction with a seal which is not formed by surfaces integral with the tube and the fitting. Such an embodiment is shown in FIG. 4, wherein a separate seal 88 is positioned between the end fitting 22 (or 24, not shown) and the tube 12. Such seals may have square cross sections as shown to operate as an "extrusion" type seal which seals more tightly without overstressing the seal material when subjected to increased pressure. Such seals are advantageously formed of plastic materials such as PEEK as well as perfluoroelastomeric materials marketed under the trade names CHEMRAZ and KALREZ.

Figure 5:
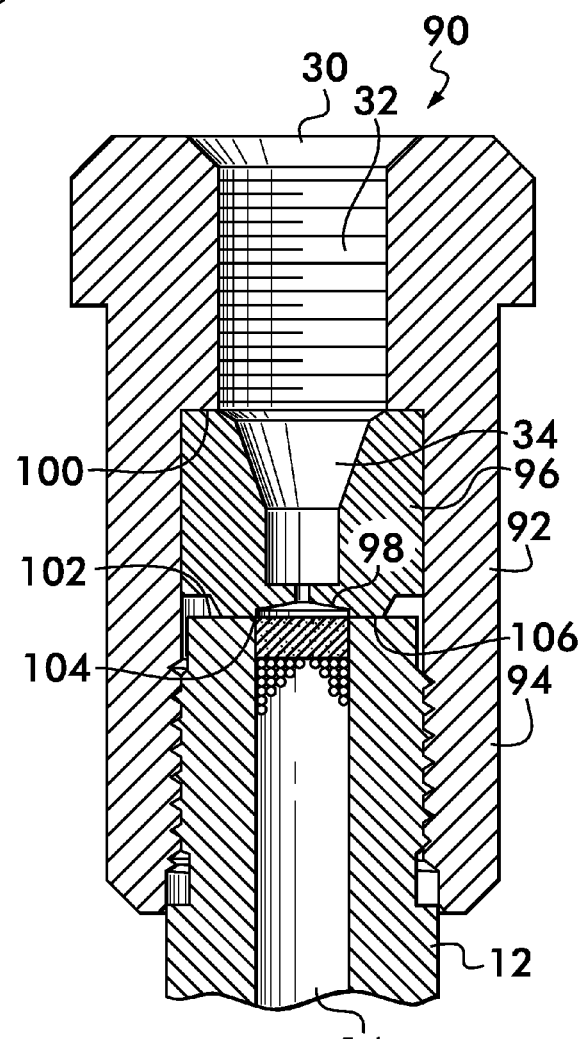

Yet another embodiment of the column 90 according to the invention is shown in FIG. 5, wherein one or both of the end fittings 92 is comprised of two components, a compression nut 94 threadedly attached to the tube 12, and a compression body 96 in which a duct 98, which could be an inlet or an outlet duct as described above, is located. Compression body 96 is captured between an axially facing surface 100 on the compression nut 94 and a surface 102 on tube 12 which surrounds the bore 14 at the end of the tube 12. Column embodiment 90 features the metal to metal seal as described above, the compression body 96 having the sealing surface 106 which engages the surface 102 on the tube to effect the seal when the compression nut is tightened. Similar to the embodiments described above, end fitting 92 has the port 30 with the internal threads 32 and tapered section 34 to effect a sealed connection with a capillary tube to connect the column to a chromatograph (not shown).

Figure 6:
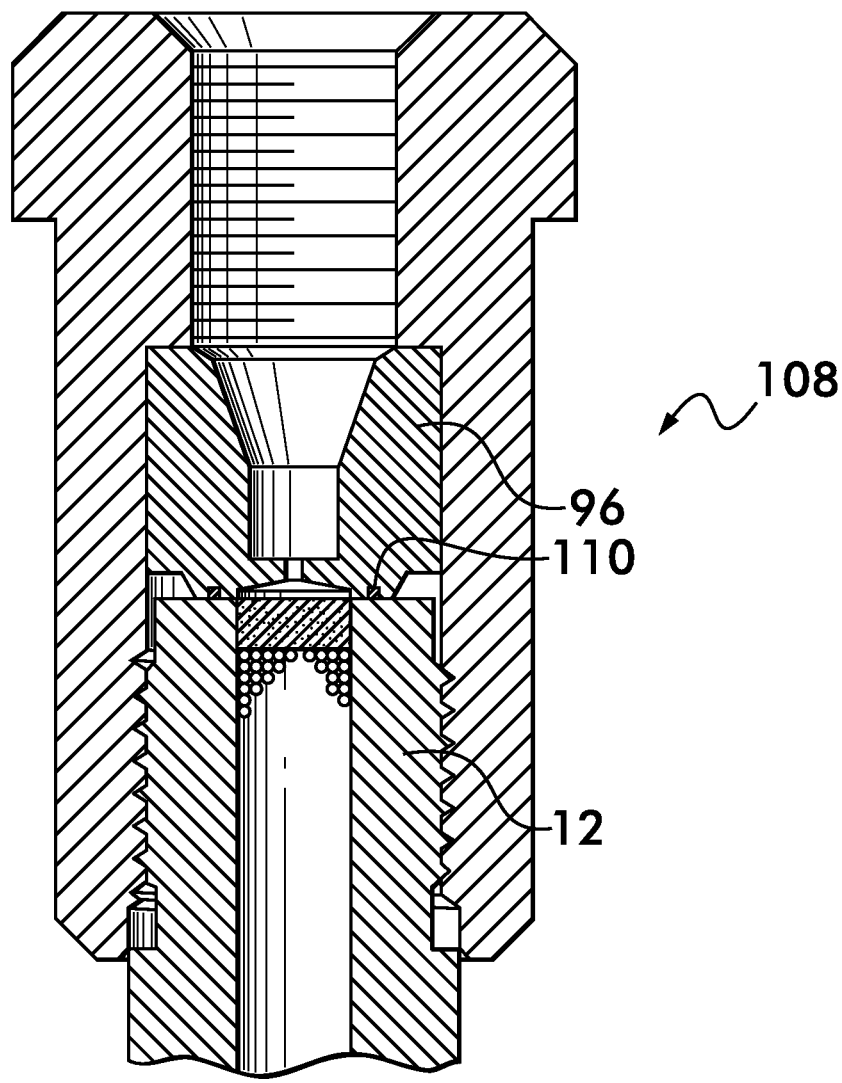

A further embodiment of the column 108 is shown in FIG. 6, wherein a separate seal 110 is positioned between the compression body 96 and the tube 12. Again, the seal 110 may be an extrusion type seal of perfluoroelastomeric material compressed between the compression body and the tube as the compression nut is tightened.

Liquid chromatographic columns having end fittings according to the invention as described herein are expected to have improved performance over columns according to the prior art as manifest by narrower chromatogram peaks leading to greater resolution capability.

What is claimed is:

1. A column for chromatography, said column comprising:
a tube having a bore therethrough, said bore having a diameter;
a first porous plug located within said bore at a first end of said tube;
a first fitting attached to said first end of said tube, said first fitting having a duct positioned therein, said duct having a first opening in facing relation with said first porous plug, said first opening having a diameter at least about equal to said bore diameter, said first opening being positioned within a recess in said first fitting and in spaced apart relation away from said first porous plug, said first fitting comprising a first sealing surface integrally formed therewith and surrounding said recess, a second sealing surface integrally formed with said tube and surrounding said bore at said first end of said tube, said first sealing surface contacting said second sealing surface and forming a seal between said first fitting and said tube.

2. The column according to claim 1, wherein said duct has a second opening positioned in spaced apart relation to and facing said first opening, said second opening having a diameter less than said diameter of said first opening.

3. The column according to claim 2, wherein said duct comprises a conical surface positioned between said first and second openings.

4. The column according to claim 3, wherein said conical surface has a cone angle from about 150° to about 175°.

5. The column according to claim 2, wherein said first fitting further comprises a conduit in fluid communication with said second opening, said conduit having an inner diameter about equal to said diameter of said second opening.

6. The column according to claim 1, wherein said first fitting is theadedly attached to said tube.

7. The column according to claim 1, wherein said first duct is integrally formed with said first fitting.

8. The column according to claim 1 further comprising:
a second porous plug located within said bore at a second end of said tube;
a second fitting attached to said second end of said tube, said second fitting having a second duct positioned therein, said second duct having a first opening in facing relation with said second porous plug, said first opening of said second duct having a diameter at least about equal to said bore diameter, said first opening of said second duct being positioned within a recess in said second fitting and in spaced apart relation away from said second porous plug.

9. The column according to claim 8, wherein said second duct has a second opening positioned in spaced apart relation to and facing said first opening of said second duct, said second opening of said second duct having a diameter less than said diameter of said first opening of said second duct.

10. The column according to claim 9, wherein said second duct comprises a conical surface positioned between said first and second openings.

11. The column according to claim 10, wherein said conical surface has a cone angle from about 150° to about 175°.

12. The column according to claim 9, wherein said second fitting further comprises a second conduit in fluid communication with said second opening, said second conduit having an inner diameter about equal to said diameter of said second opening.

13. The column according to claim 1, further comprising a packing medium located within said bore.

14. A column for chromatography, said column comprising:
a tube having a bore with a bore inlet at one end and a bore outlet at an opposite end;
a first porous plug positioned within said bore at said one end;
a second porous plug positioned within said bore at said opposite end;
a packing medium contained within said bore,
a first fitting attached to said tube at said one end, said first fitting having a first duct positioned therein in fluid communication with said bore inlet, said first duct having an outlet facing said bore inlet, said outlet having a diameter at least about equal a diameter of said bore, said outlet being positioned within a recess in said first fitting in spaced apart relation away from said first porous plug, said first fitting comprising a first sealing surface integrally formed therewith and surrounding said recess, a second sealing surface integrally formed with said tube and surrounding said bore inlet, said first sealing surface contacting said second sealing surface and forming a seal between said first fitting and said tube;
a second fitting attached to said tube at said opposite end, said second fitting having a second duct positioned therein in fluid communication with said bore outlet, said second duct having an inlet facing said bore outlet, said inlet having a diameter at least about equal to a diameter of said bore, said inlet being positioned within a recess in said second fitting in spaced relation away from said second porous plug.

15. The column according to claim 14, wherein said first duct comprises a first conical surface and said second duct comprises a second conical surface.

16. The column according to claim 14, wherein said first and second fittings are threadedly attached to said tube.

17. The column according to claim 14, wherein said first duct is integrally formed with said first fitting and said second duct is integrally formed with said second fitting.

18. The column according to claim 14, wherein said second fitting comprises a third sealing surface integrally formed therewith and surrounding said recess in said second fitting, a fourth sealing surface integrally formed with said tube and surrounding said bore outlet, said third sealing surface contacting said fourth sealing surface and forming a seal between said second fitting and said tube.

* * * * *

UNITED STATES PATENT AND TRADEMARK OFFICE
CERTIFICATE OF CORRECTION

| | | |
|---|---|---|
| PATENT NO. | : 8,936,723 B2 | Page 1 of 1 |
| APPLICATION NO. | : 12/552837 | |
| DATED | : January 20, 2015 | |
| INVENTOR(S) | : Mark A. Nickerson et al. | |

It is certified that error appears in the above-identified patent and that said Letters Patent is hereby corrected as shown below:

In the Claims,

In column 6, line 67, in claim 6, delete "theadedly" and insert -- threadedly --, therefor.

In column 8, line 5, in claim 14, after "equal" insert -- to --.

Signed and Sealed this
Twenty-third Day of June, 2015

Michelle K. Lee
*Director of the United States Patent and Trademark Office*